United States Patent
Nakabayashi et al.

(10) Patent No.: US 11,694,767 B2
(45) Date of Patent: Jul. 4, 2023

(54) METHOD FOR SEARCHING FOR MOLECULAR STABLE STRUCTURE, PROGRAM FOR SEARCHING FOR MOLECULAR STABLE STRUCTURE, AND DEVICE FOR SEARCHING FOR MOLECULAR STABLE STRUCTURE

(71) Applicant: FUJIFILM Corporation, Tokyo (JP)

(72) Inventors: Jun Nakabayashi, Ashigarakami-gun (JP); Shino Ohira, Ashigarakami-gun (JP); Kyosuke Tsumura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 205 days.

(21) Appl. No.: 16/952,210

(22) Filed: Nov. 19, 2020

(65) Prior Publication Data
US 2021/0090685 A1 Mar. 25, 2021

Related U.S. Application Data

(63) Continuation of application No. PCT/JP2019/018232, filed on May 7, 2019.

(30) Foreign Application Priority Data

May 29, 2018 (JP) ................ 2018-102416

(51) Int. Cl.
*G16B 15/00* (2019.01)
*G16C 20/30* (2019.01)
*G06N 7/01* (2023.01)

(52) U.S. Cl.
CPC ............. *G16B 15/00* (2019.02); *G06N 7/01* (2023.01); *G16C 20/30* (2019.02)

(58) Field of Classification Search
CPC ......... G16B 15/00; G06N 7/005; G16C 20/30
See application file for complete search history.

(56) References Cited

U.S. PATENT DOCUMENTS

| 2010/0191517 A1 | 7/2010 | Blundell et al. |
| 2011/0137617 A1 | 6/2011 | Desmet et al. |
| 2020/0321081 A1* | 10/2020 | Tanida ............... G16B 15/30 |

FOREIGN PATENT DOCUMENTS

| JP | 2010-257297 A | 11/2010 |
| JP | 2010-539580 A | 12/2010 |

(Continued)

OTHER PUBLICATIONS

Dorn et al., "Three-dimensional protein structure prediction: Methods and computational strategies," Computational Biology and Chemistry, vol. 53, 2014, pp. 251-276, 26 pages total.

(Continued)

*Primary Examiner* — Walter L Lindsay, Jr.
*Assistant Examiner* — Geoffrey T Evans
(74) *Attorney, Agent, or Firm* — Birch, Stewart, Kolasch & Birch, LLP

(57) ABSTRACT

Provided are a method for searching for a molecular stable structure, a program for searching for a molecular stable structure, and a device for searching for a molecular stable structure, which are capable of acquiring a stable structure and various locally stable structures from a structural formula of a compound in a short time and with high accuracy. A three-dimensional structure is generated from the structural formula of the compound, and a locally stable structure is obtained from the three-dimensional structure. A one-dimensional or multidimensional energy distribution function for one or a plurality of internal coordinates and a probability distribution function of increasing a probability of low-energy internal coordinates are calculated from internal coordinates and an energy value of the locally stable (Continued)

structure. The method for searching for a molecular stable structure repeats the following processes: generating a three-dimensional structure based on the calculated probability distribution function; acquiring a locally stable structure; reflecting internal coordinates and an energy value of the obtained locally stable structure on the energy distribution function and the probability distribution function; and acquiring the locally stable structure, thereby obtaining a plurality of the locally stable structures and a structure with lowest energy. The program and the device for searching for a molecular stable structure execute the method.

11 Claims, 19 Drawing Sheets

(56) References Cited

FOREIGN PATENT DOCUMENTS

| | | | |
|---|---|---|---|
| JP | 2012-32908 | A | 2/2012 |
| JP | 5555630 | B2 | 7/2014 |

OTHER PUBLICATIONS

Extended European Search Report for corresponding European Application No. 19810911.8, dated Jul. 15, 2021.
Molloy et al., "Probabilistic Search and Energy Guidance for Biased Decoy Sampling in Ab Initio Protein Structure Prediction," IEEE/ACM Transactions on Computational Biology and Bioinformatics, vol. 10, No. 5, 2013, pp. 1162-1175, 14 pages total.
Pickard et al., "Ab initio random structure searching," Journal of Physics: Condensed Matter, vol. 23, 2011, 24 pages total.
International Preliminary Report on Patentability and Written Opinion of the International Searching Authority (Forms PCT/IB/326, PCT/IB/373 and PCT/ISA/237) for International Application No. PCT/JP2019/018232, dated Dec. 10, 2020, with an English translation.
International Search Report (Form PCT/ISA/210) for International Application No. PCT/JP2019/018232, dated Jun. 4, 2019, with an English translation.
URL: http://www.conflex.co.jp/, Conflex High Performance Conformation Analysis, retrieved on Oct. 7, 2020, 2 pages total.

* cited by examiner

FIG. 19
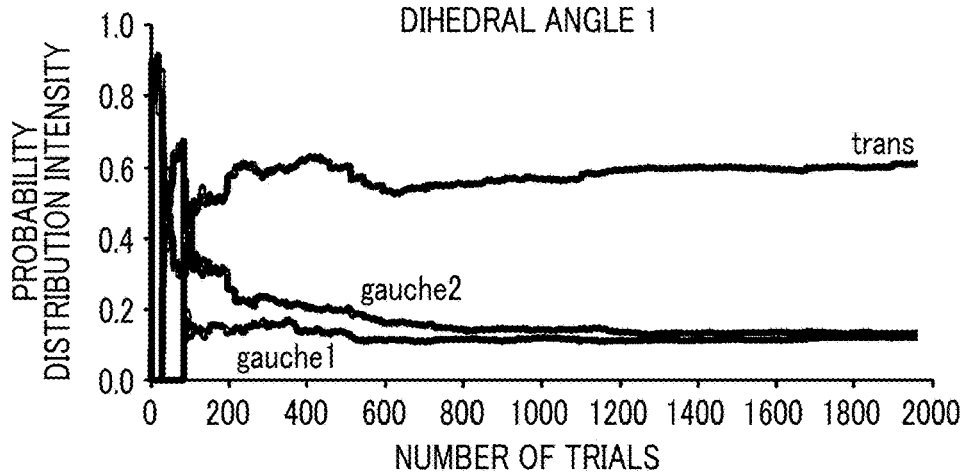
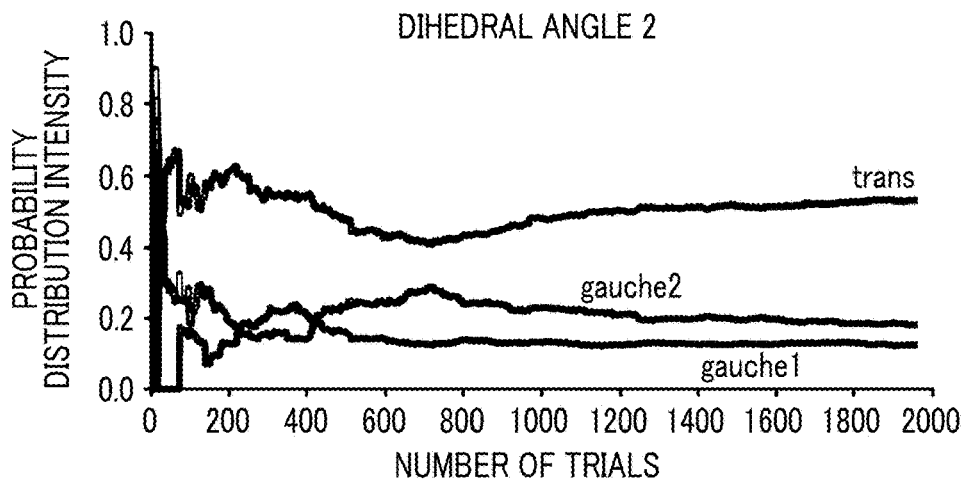
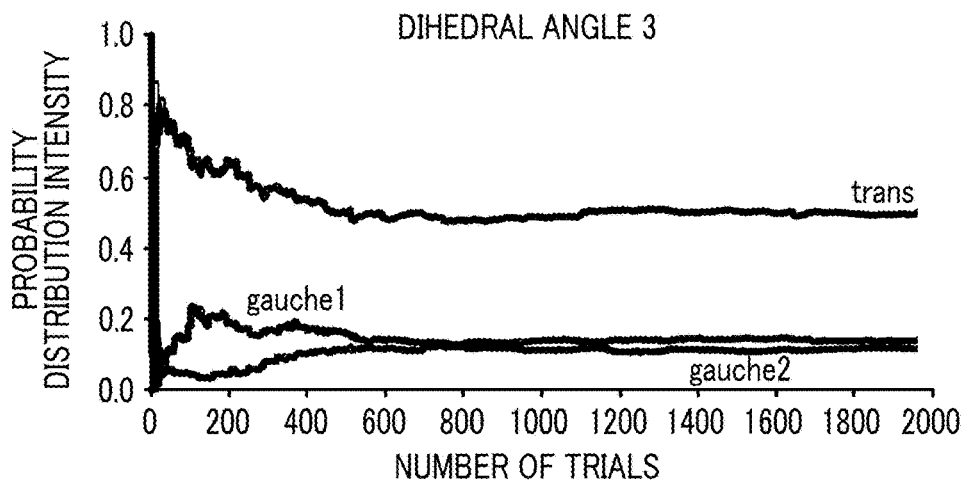

METHOD FOR SEARCHING FOR MOLECULAR STABLE STRUCTURE, PROGRAM FOR SEARCHING FOR MOLECULAR STABLE STRUCTURE, AND DEVICE FOR SEARCHING FOR MOLECULAR STABLE STRUCTURE

CROSS-REFERENCE TO RELATED APPLICATIONS

The present application is a Continuation of PCT International Application No. PCT/JP2019/018232 filed on May 7, 2019 claiming priority under 35 U.S.C § 119(a) to Japanese Patent Application No. 2018-102416 filed on May 29, 2018. Each of the above applications is hereby expressly incorporated by reference, in its entirety, into the present application.

BACKGROUND OF THE INVENTION

1. Field of the Invention

The present invention relates to a method for searching for a molecular stable structure, a program for searching for a molecular stable structure, and a device for searching for a molecular stable structure, and particularly relates to a method for searching for a molecular stable structure, a program for searching for a molecular stable structure, and a device for searching for a molecular stable structure, the molecular stable structure being expected as a drug candidate compound.

2. Description of the Related Art

It is important to obtain an energy-stable steric structure of a compound, that is, the most stable structure and various metastable structures (locally stable structures) by computer simulation, in order to predict drug activity and cell membrane permeability. It is known that a "structure in a case of binding with a protein" which is important for drug activity and a "structure in a membrane" which is important for cell membrane permeability are more stable in a low-energy structure. However, in a case where the compound is a cyclic peptide in medium-molecule drug discovery, a large number of flexible covalent bonds are included, so that a vast number of metastable structures (which are the ultimate in energy, but unstable structures) exist. Therefore, it was difficult to discover the most stable structure and the metastable structure.

In order to solve the problem, for example, JP5555630B discloses a method for determining a three-dimensional structure that predicts a three-dimensional structure in a case where a structural formula of a compound and a result of nuclear magnetic resonance (NMR) are given. In addition, in website (http://www.conflex.co.jp/), it is disclosed that local structural deformation simulating actual thermal fluctuation of a molecule is repeated to obtain a plurality of stable conformers as a three-dimensional structure from a structural formula of a compound.

SUMMARY OF THE INVENTION

However, in the method disclosed in JP5555630B, measurement results of NMR or the like are required, so that it was not possible to predict the three-dimensional structure of a compound for which there is no measurement result. Because of the requirement for measurement results, it was difficult to predict drug activity, membrane permeability, and internal stability before synthesizing the compound. In addition, in the method disclosed in website (http://www.conflex.co.jp/), conformational search is performed by the local structural deformation simulating thermal fluctuation, so that an enormous computation time was required to obtain a conformer with large deformation. Therefore, an enormous time was required to obtain various metastable structures. In addition, since the most stable structure is obtained through several metastable structures, a further enormous time was required to obtain the most stable structure.

The present invention has been made in view of such circumstances, and an object of the present invention is to provide a method for searching for a molecular stable structure, a program for searching for a molecular stable structure, and a device for searching for a molecular stable structure, which are capable of acquiring the most stable structure and various locally stable structures from a structural formula of a compound in a shorter time and with higher accuracy than conventional one.

In order to achieve the object of the present invention, a method for searching for a molecular stable structure according to an aspect of the present invention comprises: a structural formula acquisition step of acquiring a structural formula of a compound; a first three-dimensional structure generation step of generating one or more three-dimensional structures in which internal coordinates of the structural formula are randomly set; a locally stable structure acquisition step of changing the internal coordinates of the three-dimensional structure to obtain a locally stable structure which is a structure with low energy; an energy acquisition step of obtaining internal coordinates of the locally stable structure and energy of the locally stable structure in the internal coordinates; an energy distribution function calculation step of calculating an energy distribution function which is a one-dimensional or multidimensional energy distribution function calculated for one or a plurality of internal coordinates constituting the compound and shows energy distribution of the locally stable structure with respect to the internal coordinates of the locally stable structure; a probability distribution function calculation step of calculating a probability distribution function of increasing a probability of low-energy internal coordinates from the energy distribution function; a second three-dimensional structure generation step of simultaneously changing one or more internal coordinates based on the probability distribution function and generating one or more three-dimensional structures using the determined internal coordinates; a repetition step of repeating, by using the three-dimensional structure generated in the second three-dimensional structure generation step, the locally stable structure acquisition step, the energy acquisition step, the energy distribution function calculation step, the probability distribution function calculation step, and the second three-dimensional structure generation step; and an output step of outputting one or both of a plurality of the locally stable structures obtained in the locally stable structure acquisition step and a structure with lowest energy among the plurality of locally stable structures.

In the present invention, first, the three-dimensional structure is generated from the structural formula, the internal coordinates are changed to acquire the locally stable structure, and the energy distribution function and the probability distribution function of increasing a probability of low-energy internal coordinates are calculated from the obtained locally stable structure. Then, a three-dimensional structure is generated based the probability distribution function, a locally stable structure is acquired, and internal coordinates and an energy value of the locally stable structure are reflected on the probability distribution function, whereby a probability of the internal coordinates at which a low-energy structure is obtained can be increased. Therefore, a locally stable structure with low energy can be easily acquired. Further, a locally stable structure with lower energy can be obtained by increasing the number of repetition steps. Therefore, a structure with lowest energy (most stable structure) can be acquired in a short time from a plurality of the obtained locally stable structures.

In the present invention, since structure search is performed while simultaneously changing one or more internal coordinates based on the probability distribution function instead of conformational search by local structural deformation, various locally stable structures can be obtained in a short time.

In the aspect of the present invention, it is preferable that the locally stable structure is a structure having internal coordinates in which, in a case where the internal coordinates of the three-dimensional structure are changed in a direction of decreasing the energy, the energy is not further decreased.

In the aspect, a method for acquiring the locally stable structure is defined, and a structure whose energy does not decrease due to change in structure is acquired as the locally stable structure.

In the aspect of the present invention, it is preferable that the internal coordinates are determined by a dihedral angle obtained by coordinates of four atoms.

By using the dihedral angle specified by the structure of four atoms as the internal coordinates, the three-dimensional structure can be easily specified.

In the aspect of the present invention, it is preferable that the energy distribution function calculation step is performed for all of the dihedral angles that the compound takes.

According to the aspect, by performing the energy distribution function calculation step in all of the dihedral angles, the number of repetitions of the repetition step can be reduced, and a locally stable structure with low energy can be searched for with high accuracy.

In the aspect of the present invention, it is preferable that in the probability distribution function calculation step, a function of accelerating computation is added to the probability distribution function.

According to the aspect, by adding the function of accelerating computation to the probability distribution function, in the second three-dimensional structure generation step, a three-dimensional structure having some of the internal coordinates as internal coordinates other than the obtained locally stable structure can generated. There is a possibility that a locally stable structure with lower energy is obtained by acquiring a locally stable structure from the generated three-dimensional structure.

In the aspect of the present invention, it is preferable that in the second three-dimensional structure generation step, either generating a random number and selecting internal coordinates with a highest probability distribution intensity based on the random number, or determining the internal coordinates by the probability distribution function is selected, and the three-dimensional structure is generated.

According to this aspect, in the second three-dimensional structure generation step, first, by selecting either selection of the internal coordinates with the highest probability distribution intensity or determination of the internal coordinates by the probability distribution function, the internal coordinates with low energy can be easily selected, and internal coordinates of other structures can also be selected.

In order to achieve the object of the present invention, a program for searching for a molecular stable structure according to an aspect of the present invention causes a computer to execute the method for searching for a molecular stable structure described above.

The "computer" in the present invention can be realized by using one or more various processors such as a central processing unit (CPU).

In order to achieve the object of the present invention, a device for searching for a molecular stable structure comprises: a structural formula acquisition unit that acquires a structural formula of a compound; a three-dimensional structure generation unit that generates one or more three-dimensional structures; a locally stable structure acquisition unit that changes internal coordinates of the three-dimensional structure to obtain a locally stable structure which is a structure with low energy; an energy acquisition unit that obtains internal coordinates of the locally stable structure and energy of the locally stable structure in the internal coordinates; an energy distribution function calculation unit that calculates an energy distribution function which is an energy distribution function calculated for each internal coordinate of each atom constituting the compound and shows energy distribution of the locally stable structure with respect to the internal coordinates of the locally stable structure; a probability distribution function calculation unit that calculates a probability distribution function of increasing a probability of low-energy internal coordinates from the energy distribution function; and an output unit that outputs the locally stable structure. The three-dimensional structure generation unit generates the three-dimensional structure based on the acquired structural formula of the compound or the probability distribution function.

According to the present invention, it is possible to increase a probability of the internal coordinates at which a low-energy structure is obtained in the same manner as in the above-described method for searching for a molecular stable structure, and it is possible to easily acquire a locally stable structure with low energy.

In the aspect of the present invention, it is preferable that the device further comprises: a most stable structure acquisition unit that acquires a structure with lowest energy from the locally stable structures obtained by the locally stable structure acquisition unit.

According to this aspect, it is possible to obtain a locally stable structure with low energy, and thus it is possible to easily obtain the structure with lowest energy (most stable structure) from a plurality of the obtained locally stable structures.

According to the method for searching for a molecular stable structure, the program for searching for a molecular stable structure, and the device for searching for a molecular stable structure of the aspect of the present invention, the following processes are repeated: the locally stable structure is obtained; the probability distribution function of increasing the probability of low-energy internal coordinates is calculated based on the internal coordinates and the energy of the locally stable structure; the three-dimensional structure is determined based on the probability distribution function; and the locally stable structure is obtained, so that a probability that a locally stable structure with low energy is obtained can be increased. Therefore, by acquiring the most stable structure from the obtained locally stable structure, the most stable structure (stable structure) and various locally stable structures (metastable structure) can be obtained in a short time and with high accuracy.

BRIEF DESCRIPTION OF THE DRAWINGS

FIG. 19 is a graph showing changes in probability distribution intensities of a trans type and a gauche type according to the number of repetitions.

DESCRIPTION OF THE PREFERRED EMBODIMENTS

Hereinafter, a method for searching for a molecular stable structure, a program for searching for a molecular stable structure, and a device for searching for a molecular stable structure according to an embodiment of the present invention will be described with reference to the accompanying drawings.

<<Device for Searching for Molecular Stable Structure>>

Figure 1:
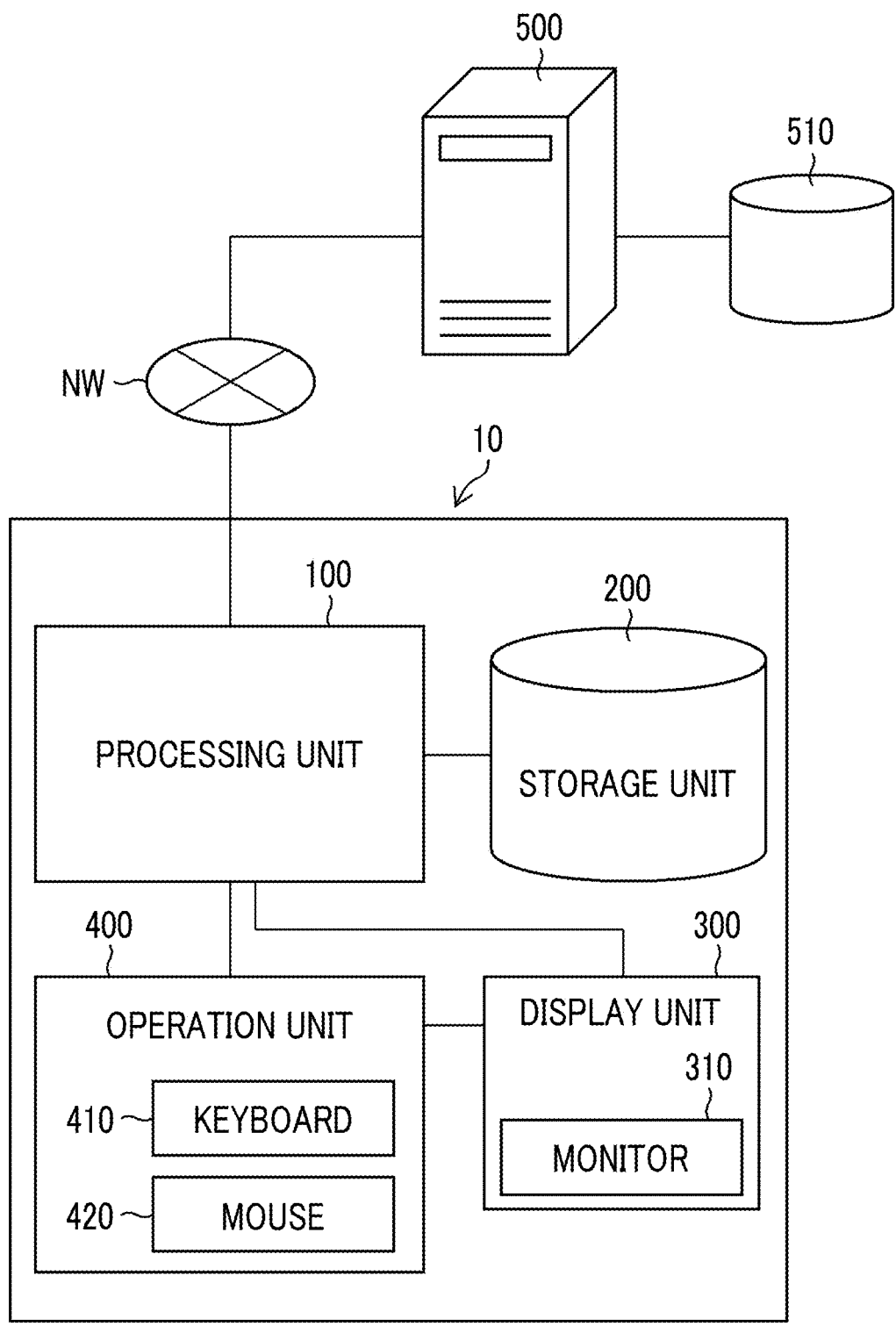
FIG. 1 is a block diagram showing a configuration of a device for searching for a molecular stable structure.

FIG. 1 is a block diagram showing a configuration of a device for searching for a molecular stable structure (hereinafter, simply referred to as a "search device") 10. The search device 10 is a device for searching for a stable structure (locally stable structure and most stable structure) from a compound (target structure), and can be realized by using a computer. As shown in FIG. 1, the search device 10 comprises a processing unit 100, a storage unit 200, a display unit 300, and an operation unit 400, which are connected to one another to transmit and receive necessary information. Various installation forms can be adopted for these constituent elements, and each constituent element may be installed in one location (in one housing or in one room), or may be installed in a remote location and connected via a network. In addition, the search device 10 is connected to an external server 500 and an external database 510 via a network NW such as the Internet, and can acquire information such as a structural formula of a compound as necessary.

<Configuration of Processing Unit>

Figure 2:
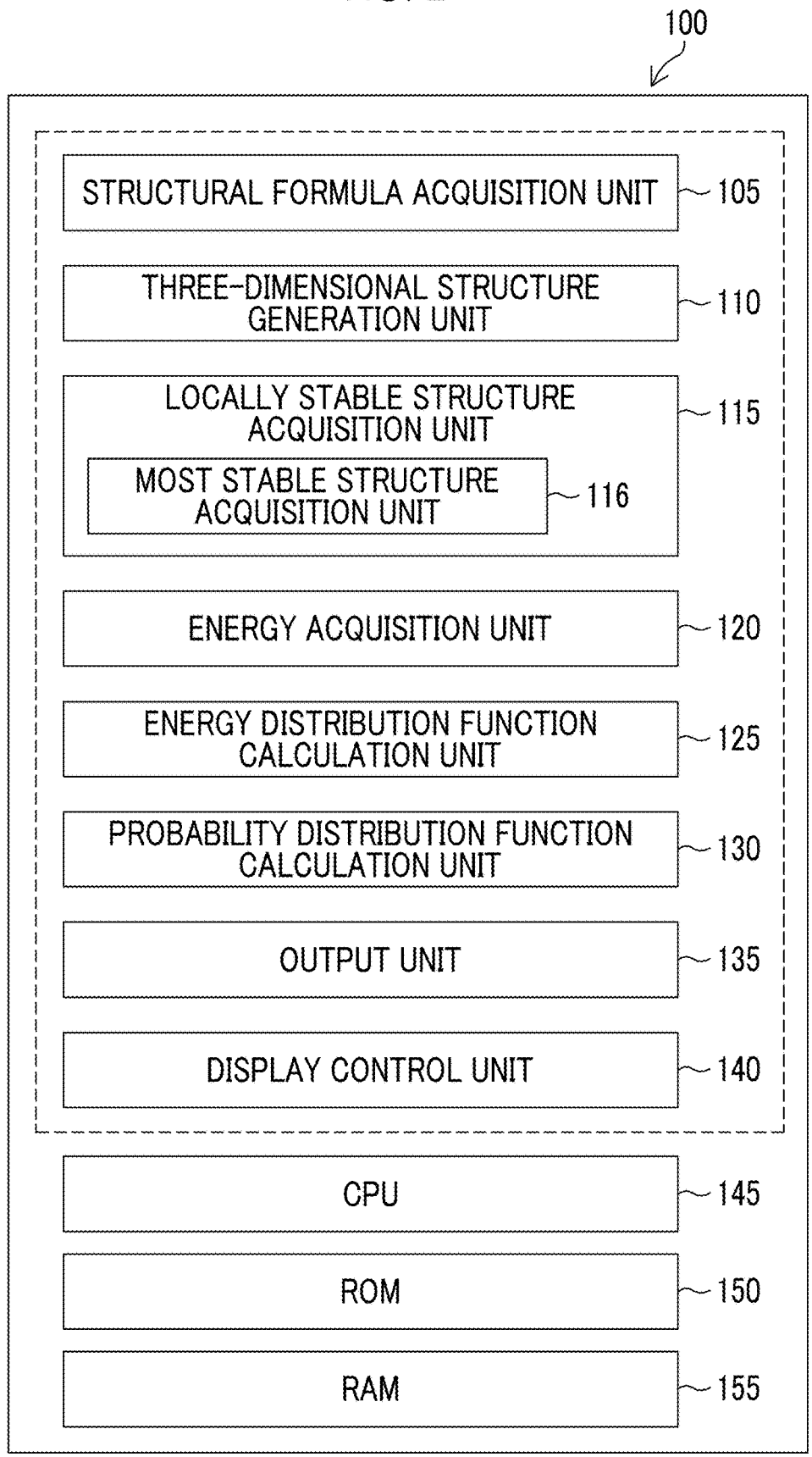
FIG. 2 is a diagram showing a configuration of a processing unit.

FIG. 2 is a diagram showing a configuration of the processing unit 100. The processing unit 100 comprises a structural formula acquisition unit 105, a three-dimensional structure generation unit 110, a locally stable structure acquisition unit 115, an energy acquisition unit 120, an energy distribution function calculation unit 125, a probability distribution function calculation unit 130, an output unit 135, a display control unit 140, a central processing unit (CPU) 145, a read only memory (ROM) 150, and a random access memory (RAM) 155. The locally stable structure acquisition unit 115 comprises a most stable structure acquisition unit 116.

The structural formula acquisition unit 105 acquires information such as a structural formula of a compound via a recording medium interface such as a DVD drive and a semiconductor memory terminal (not shown), and/or a network. The three-dimensional structure generation unit 110 randomly sets internal coordinates of the structural formula from the structural formula of the compound acquired by the structural formula acquisition unit 105, and generates one or more three-dimensional structures. In addition, the internal coordinates are determined based on a probability distribution function described below, and one or more three-dimensional structures are generated. The locally stable structure acquisition unit 115 changes the internal coordinates of the three-dimensional structure generated by the three-dimensional structure generation unit 110 and locally deforms the structure to acquire a locally stable structure which is a structure with low energy. Specifically, the locally stable structure is a structure in which even though the structure is deformed so that the energy is decreased, the energy is not further decreased. Further, the locally stable structure acquisition unit 115 comprises the most stable structure acquisition unit 116 and acquires a most stable structure with lowest energy from the obtained locally stable structures. In the present specification, "energy" is energy derived from a three-dimensional structure, and does not indicate energy resulting from change of one of internal coordinates described below.

The energy acquisition unit 120 acquires the energy of the locally stable structure acquired by the locally stable structure acquisition unit 115. The energy distribution function calculation unit 125 calculates an energy distribution function showing distribution of the energy of the locally stable structure (structural energy) with respect to each of the internal coordinates of the locally stable structure. The energy distribution function is calculated for each internal coordinate constituting the compound. The probability distribution function calculation unit 130 calculates a probability distribution function of increasing a probability of low-energy internal coordinates from the energy distribution function.

The output unit 135 outputs the locally stable structure acquired by the locally stable structure acquisition unit 115. In addition, the output unit 115 outputs the most stable structure obtained by the most stable structure acquisition unit 116. The display control unit 140 controls display of the acquired information and a processing result on a monitor 310. Details of processing of the method for searching for a molecular stable structure using these functions of the processing unit 100 will be described below. The processing by these functions is performed under control of the CPU 145.

The function of each unit of the processing unit 100 described above can be realized by using various processors. The various processors include, for example, a CPU that is a general-purpose processor that executes software (program) to realize various functions. The various processors described above also include a programmable logic device (PLD) that is a processor of which a circuit configuration can be changed after manufacture, such as a field programmable gate array (FPGA). Further, a dedicated electric circuit that is a processor having a circuit configuration designed to be dedicated to execute specific processing, such as an application specific integrated circuit (ASIC), is also included in the various processors described above.

The function of each unit may be realized by one processor, or may be realized by combining a plurality of processors. In addition, a plurality of functions may be realized by one processor. As an example in which the plurality of functions are configured by one processor, first, as represented by a computer such as a client or a server, one processor is configured by a combination of one or more CPUs and software and this processor functions as the plurality of functions. Second, as represented by a system on chip (SoC), a processor that realizes the functions of the entire system by using one integrated circuit (IC) chip is used. In this way, the various functions are configured by using one or more of the various processors described above as a hardware structure. Further, the hardware structure of these various processors is more specifically an electric circuit (circuitry) in which circuit elements such as semiconductor elements are combined.

In a case where the processor or the electric circuit described above executes software (program), a processor (computer) readable code of the software to be executed is stored in a non-transitory recording medium such as the ROM 150 (see FIG. 2), and the processor refers to the software. The software stored in the non-transitory recording medium includes a program for executing a method for calculating a molecular stable structure according to the present invention. The code may be recorded in a non-temporary recording medium such as various magneto-optical recording devices and a semiconductor memory, instead of the ROM 150. In processing using software, for example, the RAM 155 is used as a temporary storage area, and data stored in, for example, an electronically erasable and programmable read only memory (EEPROM) (not shown) can be referred to.

<Configuration of Storage Unit>

Figure 3:
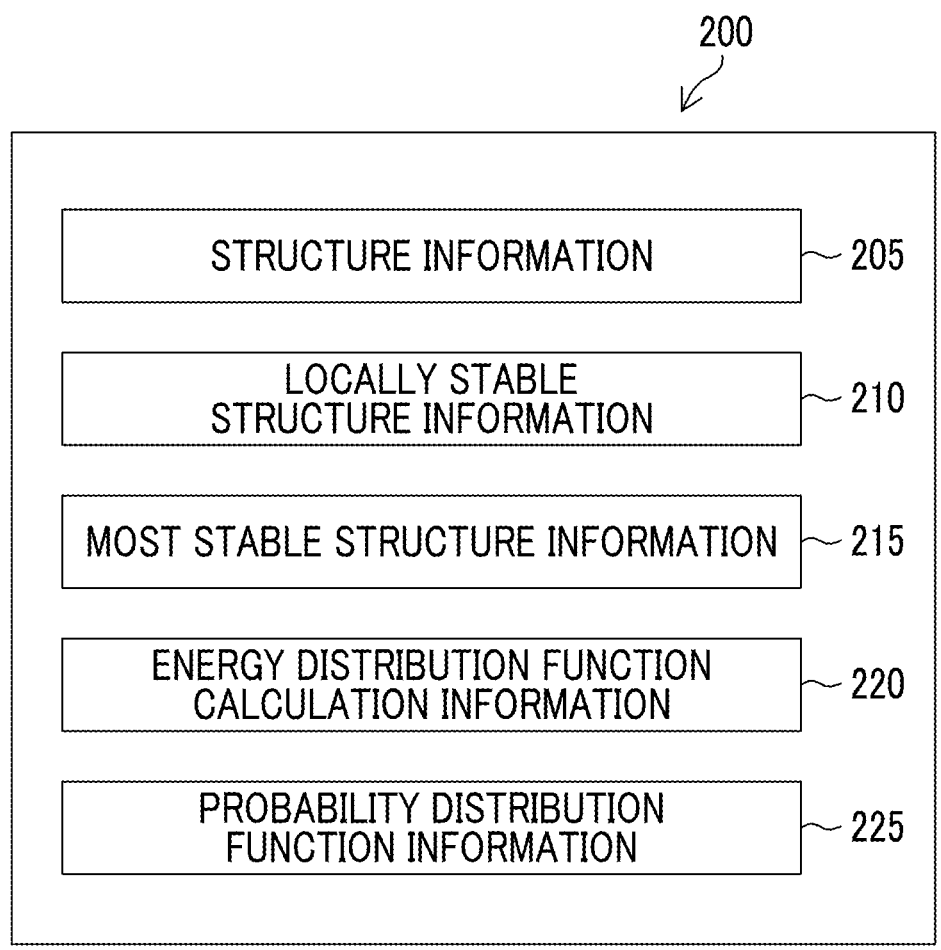
FIG. 3 is a diagram showing information stored in a storage unit.

The storage unit 200 is configured of a non-transitory recording medium such as a digital versatile disk (DVD), a hard disk, or various semiconductor memories, and a controller thereof, and stores an image and information shown in FIG. 3. Structure information 205 includes the structural formula of the compound. Locally stable structure information 210 includes three-dimensional structure information (internal coordinate information) of a locally stable structure obtained by changing the internal coordinates of the three-dimensional structure generated from the structure information 205 and information on an energy value thereof. Further, the locally stable structure information 210 includes three-dimensional structure information (internal coordinate information) of a locally stable structure obtained by changing the internal coordinates of the three-dimensional structure generated from the probability distribution function and information on an energy value thereof. Most stable structure information 215 includes three-dimensional structure information (internal coordinate information) of a most stable structure which is a structure having lowest energy among the locally stable structures and information on an energy value thereof. Energy distribution function information 220 includes, for one internal coordinate of the locally stable structure, an energy distribution function showing distribution of the energy of the locally stable structure (structural energy) with respect to the internal coordinate. Probability distribution function information 225 includes, for one internal coordinate, a probability distribution function of increasing a probability of low-energy internal coordinates. The energy distribution function information 220 and the probability distribution function information 225 include the energy distribution function and the probability distribution function calculated for each of internal coordinates of atoms constituting the compound. In addition, a locally stable structure is acquired from the three-dimensional structure generated by the probability distribution function and internal coordinates and energy of the obtained locally stable structure are reflected on the energy distribution function and the probability distribution function, whereby an energy distribution function and a probability distribution function with high accuracy are obtained. The energy distribution function information 220 and the probability distribution function information 225 also include an energy distribution function and a probability distribution function that reflect the internal coordinates and the energy of these locally stable structures.

<Configuration of Display Unit and Operation Unit>

The display unit 300 comprises the monitor 310 (display device), and can display an input image, an image and information stored in the storage unit 200, a result of the processing by the processing unit 100, and the like. The operation unit 400 includes a keyboard 410 and a mouse 420 as an input device and/or a pointing device, and a user can perform operations necessary for executing the method for searching for a molecular stable structure according to the present embodiment through these devices and a screen of the monitor 310. The operations that can be executed by the user include input of a structural formula of a compound, designation of a threshold value in calculating a probability distribution function, designation of a threshold value in generating a three-dimensional structure using a probability distribution function, and the like.

<Processing in Device for Searching for Molecular Stable Structure>

The above-described device for searching for a molecular stable structure search device 10 can search for a molecular stable structure in accordance with a user's instruction through the operation unit 400.

<<Searching for Molecular Stable Structure>>

Figure 4:
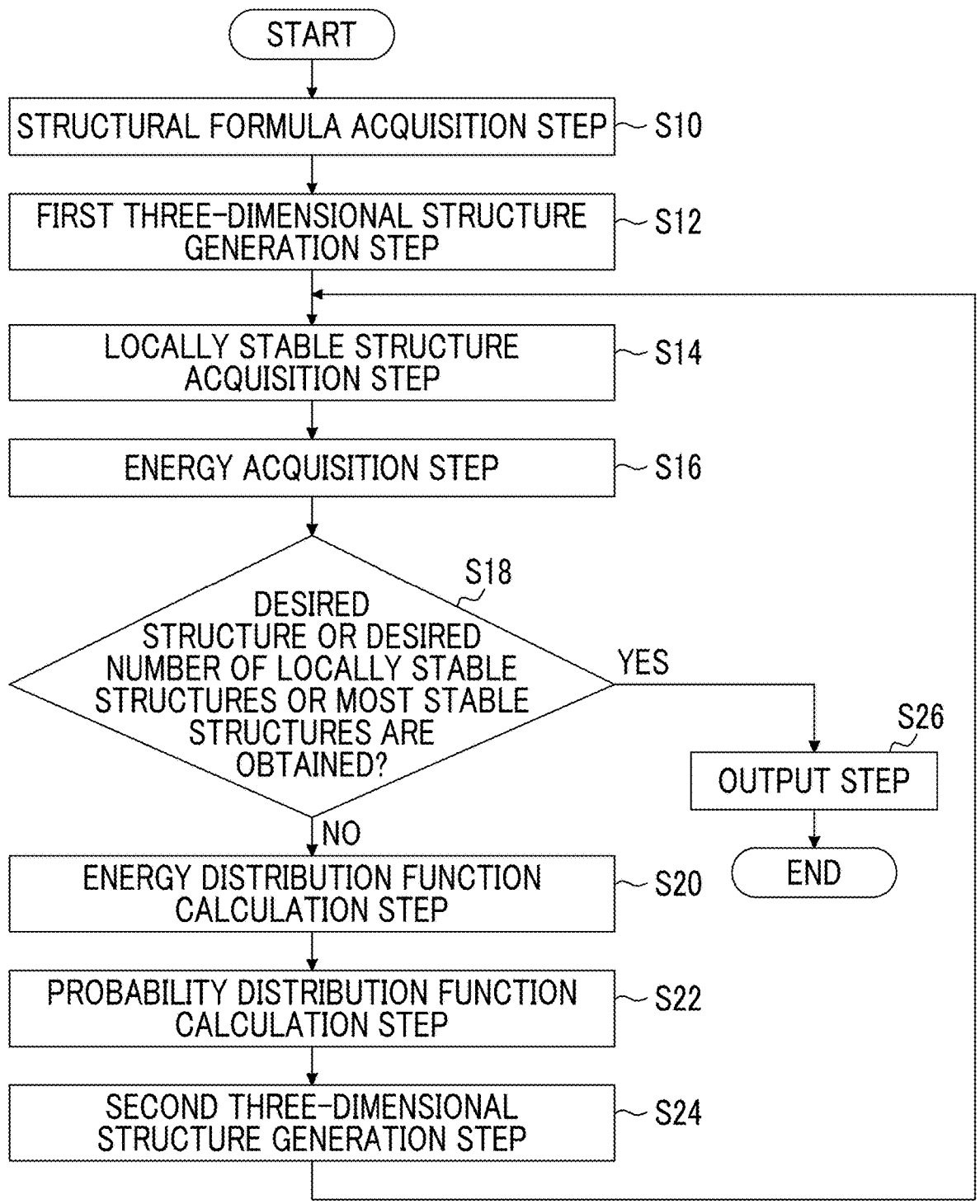
FIG. 4 is a flowchart showing a method for searching for a molecular stable structure.

FIG. 4 is a flowchart showing the method for searching for a molecular stable structure of a compound. The method for searching for a molecular stable structure includes: a structural formula acquisition step (Step S10) of acquiring a structural formula of a compound; a first three-dimensional structure generation step (step S12) of generating one or more three-dimensional structures in which internal coordinates of the structural formula are randomly set; a locally stable structure acquisition step (step S14) of obtaining a locally stable structure from the generated three-dimensional structure; an energy acquisition step (step S16) of obtaining an energy (structural energy) value of the locally stable structure and internal coordinates of each atom of the locally stable structure; and a step (step S18) of determining whether or not a desired structure or a desired number of locally stable structures or most stable structures are obtained.

In a case where determination is made in step S18 that a desired structure or a desired number of the locally stable structures or the most stable structures are not obtained, the method includes: an energy distribution function calculation step (step S20) of calculating an energy distribution function showing energy distribution of the locally stable structure with respect to the internal coordinates of the locally stable structure in each internal coordinate; a probability distribution function calculation step (step S22) of calculating a probability distribution function of increasing a probability of low-energy internal coordinates from the energy distribution function; and a second three-dimensional structure generation step (step S24) of generating one or more three-dimensional structures based on the probability distribution function.

The energy distribution function may calculate a one-dimensional energy distribution function for each internal coordinate constituting a compound, and may calculate a two-dimensional energy distribution function using two internal coordinates or a multidimensional energy distribution function using a plurality of internal coordinates.

In the probability distribution function calculation step, it is preferable to add a function of accelerating computation to the probability distribution function. The function of accelerating computation may include, but is not limited to, a white noise described below.

After a three-dimensional structure is generated in step S24, the process returns to step S14, a locally stable structure is acquired from this three-dimensional structure, and internal coordinates and an energy value of the locally stable structure are acquired. Then, the internal coordinates and the energy value of the locally stable structure are reflected on the energy distribution function and the probability distribution function so far. By repeating step S14 to step S24, the probability distribution function obtained in step S22 can be made to be a probability distribution function having a high probability of the internal coordinates for obtaining low energy. Then, by using this probability distribution function, a probability that a locally stable structure with lower energy can be obtained can be increased.

In a case where determination is made in step S18 that a desired structure or a desired number of the locally stable structures or the most stable structures are obtained, the method includes an output step (step S26) of outputting one of a plurality of the obtained locally stable structures or the most stable structure with lowest energy among the locally stable structures. By repeating processing from step S14 to step S24, the plurality of locally stable structures can be obtained. In addition, by selecting a structure with lowest energy among the locally stable structures, the most stable structure among the obtained structures can be obtained. Although it is not possible to objectively determine whether or not the obtained most stable structure is truly the most stable except for a specific compound, the greater the number of times the processing from step S14 to step S24 are repeated, the higher the probability that the obtained most stable structure is truly the most stable. In addition, it is possible to estimate, to some extent, whether or not the obtained most stable structure is truly the most stable from a state of convergence of the probability distribution function (shown in FIG. 19 described below). A molecular stable structure can be determined by obtaining the most stable structure among the obtained structures. In addition, the plurality of locally stable structures are output, whereby, in a case where the most stable structure is not adopted as an actual steric structure of the compound, a candidate for the next steric structure can be selected from the locally stable structures.

Hereinafter, each step will be described.

<Structural Formula Acquisition Step (Step S10)>

Figure 5:
FIG. 5 shows a structural formula of dodecane ($C_{12}H_{26}$).

The structural formula acquisition step S10 is a step of acquiring a structural formula of a compound by inputting the structural formula of the compound according to a user's operation. Examples of the structure of the compound include a peptide having a plurality of amino acids bonded to one another and a molecular weight of 500 or more. In the present embodiment, in order to simplify description, dodecane ($C_{12}H_{26}$) shown in FIG. 5 will be described.

<First Three-Dimensional Structure Generation Step (Step S12)>

The first three-dimensional structure generation step S12 is a step of generating one or more three-dimensional structures from the structural formula acquired in the structural formula acquisition step S10. The three-dimensional structure can be generated by randomly setting internal coordinates of the structural formula.

The number of three-dimensional structures to be generated may be one or plural. By generating a plurality of the three-dimensional structures, it is possible to increase the number of locally stable structures obtained in the locally stable structure acquisition step S14 of the next step. Hereinafter, in order to simplify description, a case where one three-dimensional structure is generated will be described.

Figure 6:
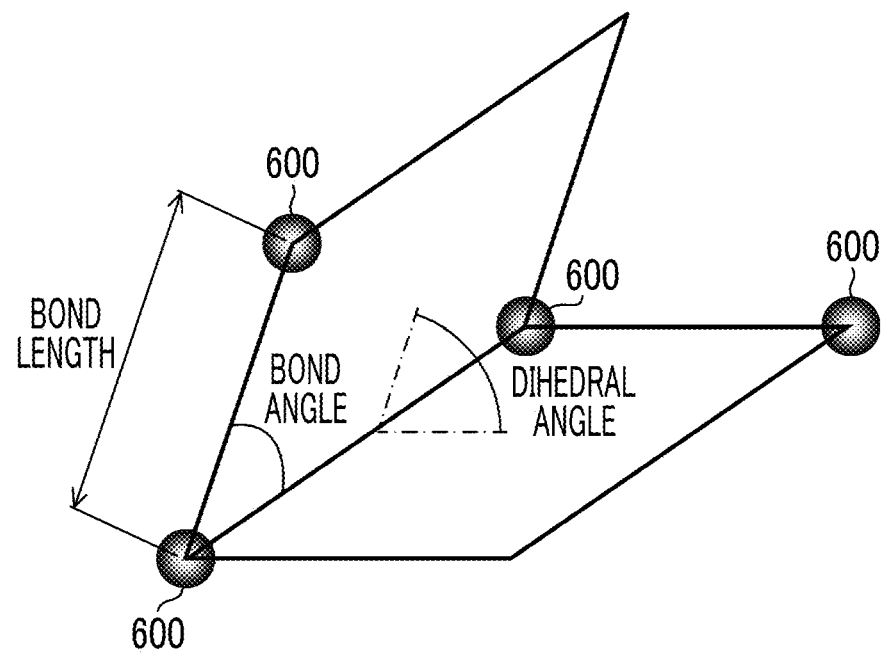
FIG. 6 is a diagram illustrating internal coordinates that determine a three-dimensional structure.

Elements that determine the three-dimensional structure include, in a case where four atoms 600 exist, a bond length determined by arrangement (coordinates) of two atoms 600, a bond angle determined by arrangement of three atoms 600, and a dihedral angle determined by arrangement of four atoms 600, as shown in FIG. 6. In the present embodiment, arrangement of atoms, that is, the internal coordinates of the structure are changed by changing a dihedral angle $\varphi$ as the internal coordinates. The dihedral angle may be a dihedral angle of atoms in which four atoms are continuously bonded as shown in FIG. 6, and a dihedral angle formed by atoms not bonded may also be used as the internal coordinates.

As another example of the internal coordinates, an interatomic distance can be used. In a case where an index of each atom is represented by a number and a distance between an atom x and an atom y is represented by $d(x,y)$, a three-dimensional structure of a molecule can be uniquely determined by the following internal coordinates.

$d(1,2)$,
$d(1,3), d(2,3)$,
$d(1,4), d(2,4), d(3,4)$,
$d(2,5), d(3,5), d(4,5), \ldots$.

Various methods are known for making the structural formula three-dimensional, and the first three-dimensional structure generation step S12 is not particularly limited and can be performed.

<Locally Stable Structure Acquisition Step (Step S14)>

Figure 7:
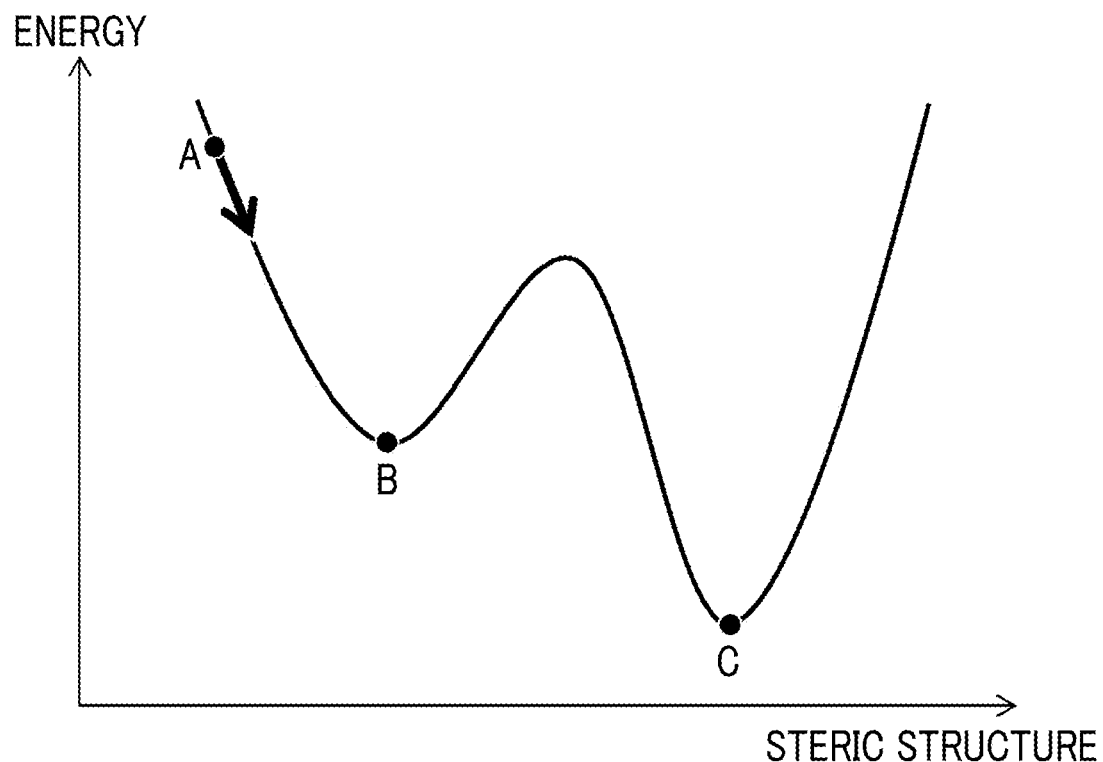
FIG. 7 is a graph schematically showing a change in energy when a steric structure is changed.

The locally stable structure acquisition step S14 is a step of acquiring a locally stable structure from the three-dimensional structure (steric structure) obtained in the first three-dimensional structure generation step S12. FIG. 7 is a graph schematically showing a change in energy when a steric structure is changed. As shown in FIG. 7, an energy value of a compound changes by changing a steric structure.

Figure 8:
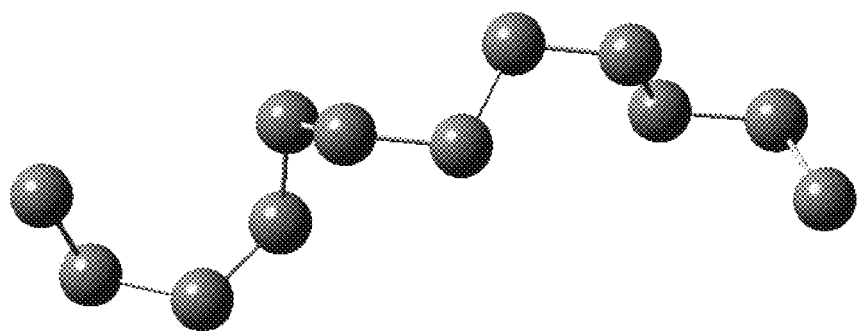
FIG. 8 is a diagram showing an example of a locally stable structure of dodecane ($C_{12}H_{26}$).

Acquisition of the locally stable structure is performed in the first three-dimensional structure generation step S12 by searching for a three-dimensional structure with low energy from the three-dimensional structure randomly generated. Acquisition of the locally stable structure can be performed as follows. In FIG. 7, a point indicating the energy of the three-dimensional structure generated in the first three-dimensional structure generation step S12 is defined as A. A slope of an energy curve (differential value of energy) at a point A (initial structure) is computed, and the structure is slightly changed in a direction of decreasing energy (arrow direction). At the changed point, the slope of the curve is computed again, and the structure is slightly changed. This step is repeated, and computation ends at the time when the energy is not further decreased even though the structure is changed. This point (point B) is a locally stable structure. FIG. 8 shows an example of the obtained locally stable structure of dodecane ($C_{12}H_{26}$). An energy value of this locally stable structure is E=−61.8925 kcal/mol.

Various methods of moving the structure can be adopted, for example, a steepest descent method, a conjugate gradient method, and a Berny method can be used, but the method is not particularly limited. Gaussian 09 and amber can be used as software which performs such a computation.

Figure 9:
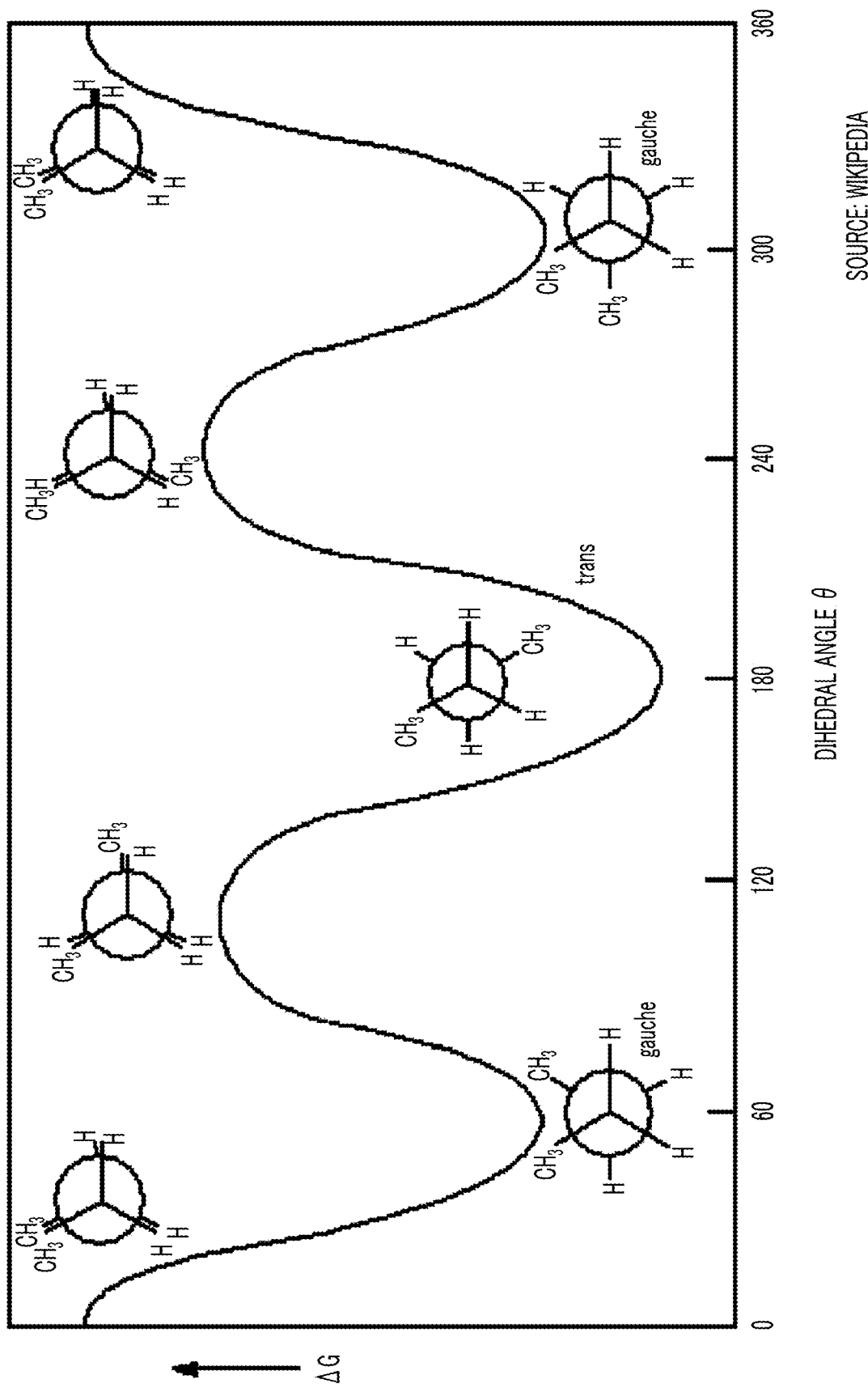
FIG. 9 is a diagram showing a relationship between a dihedral angle that a C—C—C—C bond can take and energy.

As a locally stable structure, for example, in a case of a straight-chain alkane such as dodecane ($C_{12}H_{26}$), possible locally stable structures are as follows. FIG. 9 is a diagram showing a relationship between a dihedral angle that a C—C—C—C (carbon-carbon-carbon-carbon) bond can take and energy. In a case of a straight-chain alkane, in one C—C—C—C dihedral angle, there are three locally stable structures in which an energy value is not decreased even though the dihedral angle is changed, that is, one trans type and two gauche types. In a case of dodecane, there are 12 carbons, so that there are nine dihedral angles. There are three locally stable structures for one dihedral angle, and even though these are combined, there are an enormous number of $3^9$=19683, and thus it is difficult to find the most stable structure among these locally stable structures.

As shown in FIG. 7, although there is a structure (point C: most stable structure) with lower energy than the locally stable structure (point B), the most stable structure cannot be discovered in the locally stable structure acquisition step S14 because the three-dimensional structure is locally changed. In the present embodiment, internal coordinates (dihedral angle) of the acquired locally stable structure described below and energy are reflected on the probability distribution function, whereby a probability distribution function of increasing a probability of low-energy internal coordinates is calculated, and a locally stable structure and the most stable structure with lower energy are searched for.

<Energy Acquisition Step (step S16)>

The energy acquisition step S16 is a step of acquiring the energy value of the locally stable structure obtained in the locally stable structure acquisition step S14 and each C—C—C—C dihedral angle. In the energy acquisition step S16, the energy value and each dihedral angle may be obtained from the acquired locally stable structure, but it can be acquired by performing the above-described locally stable structure acquisition step S14.

<Determination Step (Step S18)>

The determination step S18 is a step of determining whether or not a desired structure or a desired number of the locally stable structures or the most stable structures are obtained. In the present embodiment, the purpose is to acquire the most stable structure or a plurality of locally stable structures having different three-dimensional structures. Therefore, in a case where determination is made that acquisition of the locally stable structure is not necessary, such as a case where a desired structure (most stable structure) is obtained, a desired number of the most stable structures are obtained, or a desired number of the locally stable structures are obtained, the most stable structure and the locally stable structure are output (output step).

Furthermore, in a case where determination is made that acquisition of the locally stable structure is necessary, the process proceeds to the energy distribution function calculation step S20. In the following steps, a state in which one locally stable structure is acquired as a first loop will be described.

<Energy Distribution Function Calculation Step (Step S20)>

Figure 10:
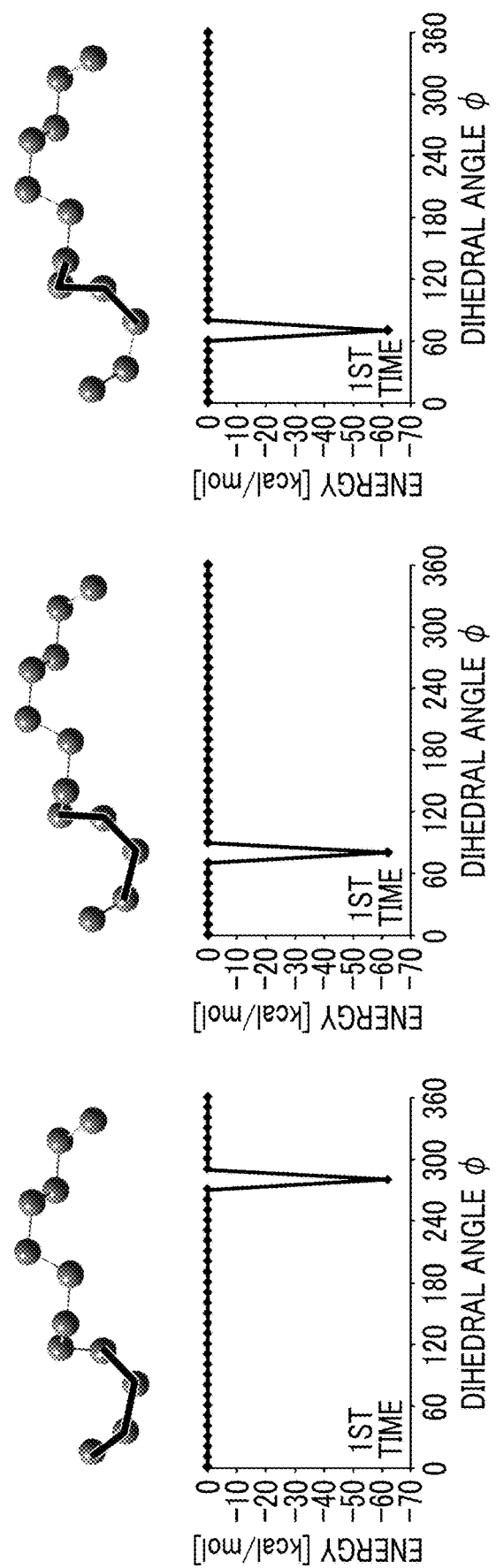
FIG. 10 is a graph showing energy with respect to a dihedral angle.

The energy distribution function calculation step S20 is a step of calculating an energy distribution function $E(\varphi)$ showing distribution of energy with respect to a dihedral angle $\varphi$. The energy distribution function $E(\varphi)$ is calculated for each dihedral angle. FIG. 10 is a graph plotting, for three dihedral angles from one end in dodecane, an energy value with respect to the dihedral angle. Since one locally stable structure is obtained, an energy peak exists at the position of the dihedral angle of the locally stable structure. Although FIG. 10 shows a graph of three dihedral angles, the energy distribution function $E(\varphi)$ is calculated for all dihedral angles (nine in a case of dodecane). In the present embodiment, although a one-dimensional energy distribution function is calculated for one dihedral angle, a multidimensional energy distribution function may be calculated for a plurality of dihedral angles.

<Probability Distribution Function Calculation Step (Step S22)>

The probability distribution function calculation step S22 is a step of calculating a probability distribution function $p(\varphi)$ for increasing a probability of low-energy dihedral angle from the energy distribution function $E(\varphi)$.

The probability distribution function $p(\varphi)$ can be obtained by the following mathematical expression.

$$p(\phi) = \frac{1}{C}\exp\left[-\frac{E(\phi) - E_{min}}{k_B T}\right], C = \int_0^{2\pi} \exp\left[-\frac{E(\phi) - E_{min}}{k_B T}\right] d\phi$$

Here, $E_{min}$ is a value with lowest energy among the structures generated so far (this is the first loop, so that there is one locally stable structure, $E_{min}$=−61.8925 kcal/mol), $k_B$ is a Boltzmann coefficient, T is an optional temperature (300K this time), and C is a normalization constant.

Figure 11:
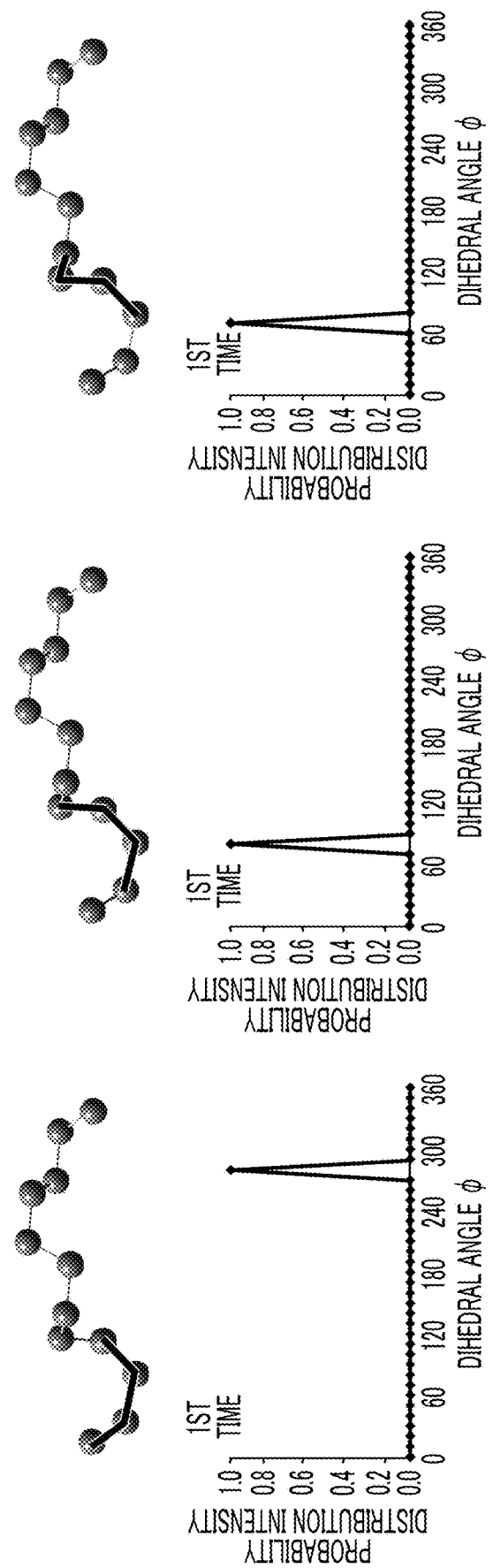
FIG. 11 is a graph showing a probability distribution function $p(\varphi)$.

FIG. 11 is a graph of the probability distribution function $p(\varphi)$ thus created. Also in the probability distribution function, one locally stable structure is obtained as in a case of the energy distribution function, and therefore, one peak exists at the position of the dihedral angle of the locally stable structure.

Next, using this probability distribution function $p(\varphi)$, one or more three-dimensional structures are generated. However, since the probability distribution function is calculated with one locally stable structure, a probability distribution intensity of one peak is 1.0, and in a case where this probability distribution function is used, one internal coordinate is selected. Therefore, it is preferable that a probability distribution function $p'(\varphi)$ added with a white noise e is calculated, and using this probability distribution function p'(φ), a three-dimensional structure is generated (second three-dimensional structure generation step S24). The probability distribution function p'(φ) added with the white noise e can be obtained by the following mathematical expression.

$$p'(\phi) = \frac{1}{C'}(p(\phi) + e)$$

$$C' = \int_0^{2\pi} (p(\phi) + e)d\phi = 1 + 2\pi e$$

$$\int_0^{2\pi} ed\phi/C' = R \Leftrightarrow e = \frac{R}{2\pi(1-R)}$$

Figure 12:
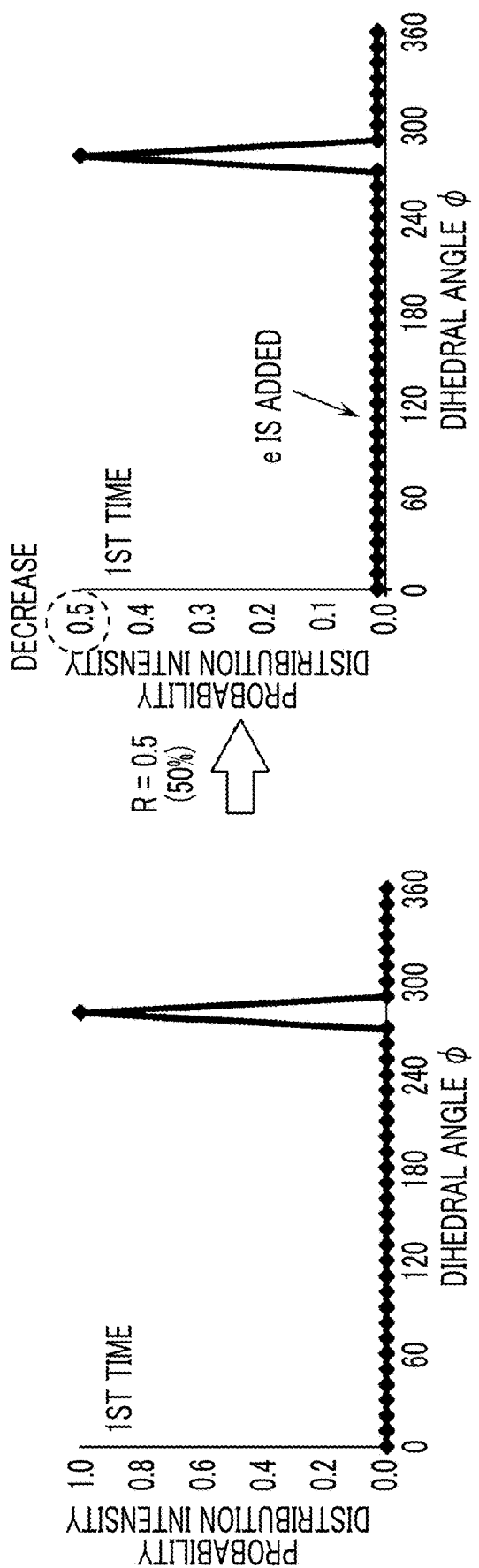
FIG. 12 is a graph showing a probability distribution function $p'(\varphi)$ added with a white noise e.

FIG. 12 shows a graph of the probability distribution function p'(φ) added with the white noise e, with R=0.5. FIG. 12 is a probability distribution function of the dihedral angle specified by the first to fourth carbons from the end of the structural formula shown in FIG. 11. As shown in FIG. 12, by adding the white noise e, it is possible to increase a probability of the dihedral angle with lowest energy and increase a probability that another dihedral angle is selected. In FIG. 12, although a graph in which computation is performed with R=0.5 is shown, a value of R can be set appropriately. In a case where it is made easy to select a dihedral angle with low energy, the value of R need only be increased, and in a case where it is made easy to select another dihedral angle, the value of R need only be decreased.

Figure 13:
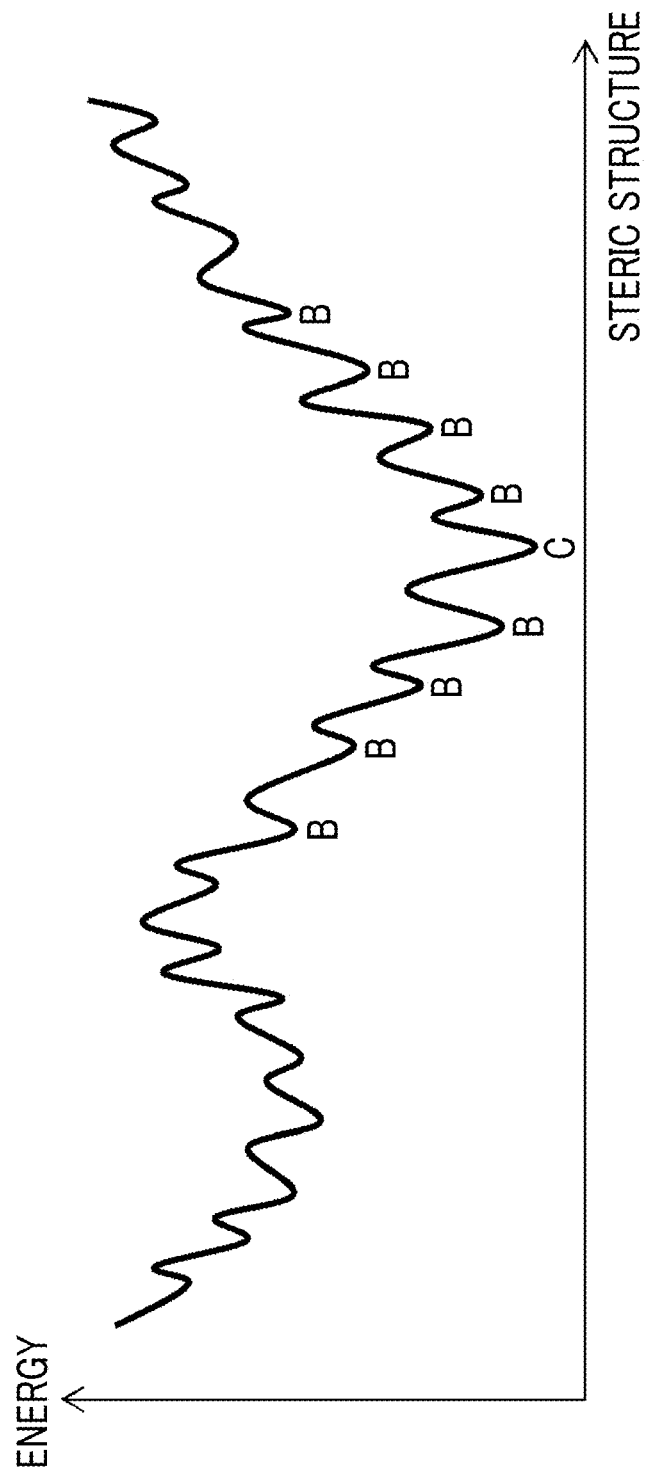
FIG. 13 is a graph schematically showing a change in energy when a steric structure is changed.

FIG. 13 is a graph schematically showing a change in energy when a steric structure is changed, and is a graph in which a range of the steric structure is larger than that of the graph of FIG. 7. As for the steric structure, as shown in FIG. 13, there are a plurality of locally stable structures in which energy values do not decrease in local structural changes (point B). Therefore, in a case where a three-dimensional structure is generated based on the probability distribution function (second three-dimensional structure generation step S24), a three-dimensional structure on a peak for which the locally stable structure has not been acquired until now can be generated by setting some of the dihedral angles to an angle different from the dihedral angle of the locally stable structure. In addition, since some of the dihedral angles are dihedral angles with low energy, it is considered to be a structure close to the locally stable structure obtained so far. As shown in FIG. 13, there is possibility that a locally stable structure with lower energy is obtained by using a close locally stable structure. A white noise need only be added appropriately, and in a case where the number of loops (repetitions) is small, a white noise can be added by reducing the value of R in order to obtain various types of locally stable structures. In a case where the number of loops (repetitions) increases and a peak exists at a dihedral angle with low energy, the value of R may be increased or a probability distribution function without addition of a white noise may be calculated.

<Second Three-Dimensional Structure Generation Step (Step S24)>

The second three-dimensional structure generation step S24 is a step of determining internal coordinates of a new three-dimensional structure based on the probability distribution function calculated in the probability distribution function calculation step S22 and generating one or more three-dimensional structures.

The method of generating a three-dimensional structure based on the probability distribution function is performed by determining each dihedral angle. First, a random number R (R is a real number which is 0 or more and 1 or less) is generated for one dihedral angle. In this case, $R_0$ is set as an appropriate threshold value. For example, $R_0$ is set to $R_0$=0.4. The generated random number R is compared with the threshold value $R_0$, and in a case of R>$R_0$, the process proceeds to (1). In addition, in a case of R≤$R_0$, the process proceeds to (2).

(1) In a case of R>$R_0$, a random number of R (R is a real number which is 0 or more and 1 or less) is generated again, and a dihedral angle is computed from the following mathematical expression. In this case, a plurality of dihedral angles can be selected by generating a plurality of random numbers. By selecting the plurality of angles, a plurality of three-dimensional structures can be generated.

$$\int_0^\phi p^{(\circ)}(\phi')d\phi' = R$$

(2) In a case of R≤$R_0$, a dihedral angle at which the probability distribution function p(φ) or p'(φ) takes the maximum value is selected. In this case, since the angle is the maximum value, one angle is selected.

Figure 14:
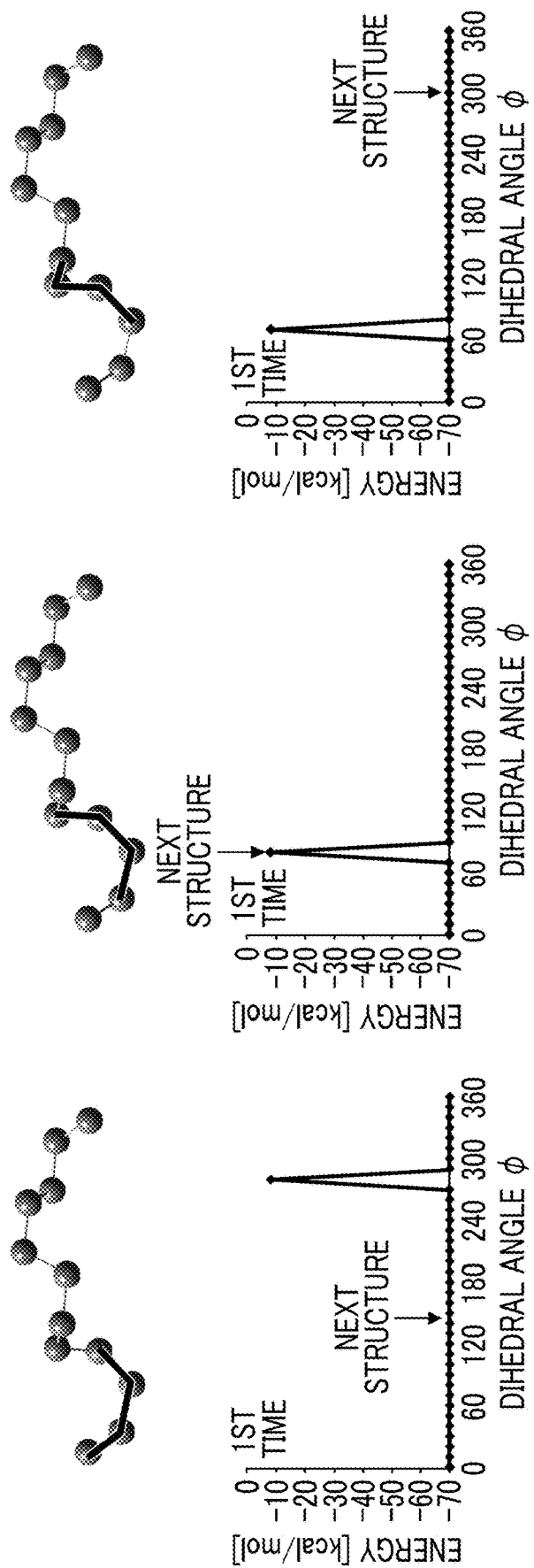
FIG. 14 is a diagram illustrating a method of selecting a dihedral angle based on a probability distribution function.

FIG. 14 is a graph showing the position of each dihedral angle of the three-dimensional structure to be generated using the above method. Although FIG. 14 also shows a graph of three dihedral angles from one end, the graph is applied to all dihedral angles. In FIG. 14, the first dihedral angle and the third dihedral angle are in a case of (1) above, and a three-dimensional structure is generated at a dihedral angle of the "next structure" shown in FIG. 14. In addition, the second dihedral angle from one end is a case of (2) above, and is an angle at which the probability distribution function takes the maximum value.

By performing selection of the dihedral angle for all dihedral angles, one or more three-dimensional structures are generated. In this way, a random number is generated, and some of the dihedral angles are set to a value at which the probability distribution function takes the maximum value, that is, to an angle with lowest energy, whereby it is possible to generate a three-dimensional structure having different peak valleys in the graph shown in FIG. 13, which is a structure close to the locally stable structure acquired so far. As shown in FIG. 13, a locally stable structure with lower energy than an adjacent locally stable structure can be obtained by changing the structure thereof. By generating a three-dimensional structure close to the locally stable structure so far, the locally stable structure obtained from this three-dimensional structure may be a locally stable structure with lower energy.

<Repetition Step>

Figure 15:
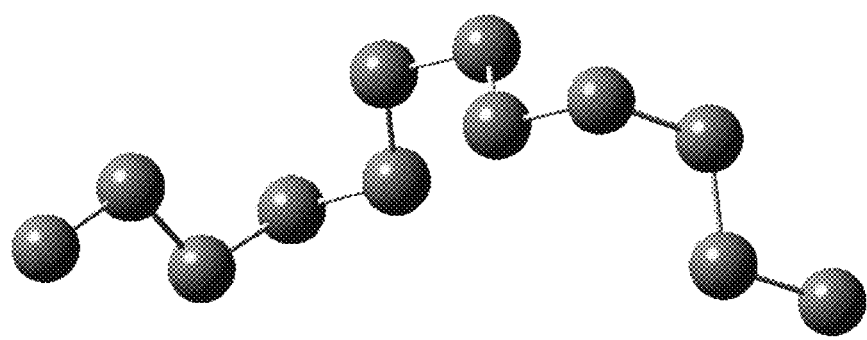
FIG. 15 is a diagram showing another example of a locally stable structure of dodecane ($C_{12}H_{26}$).

After one or more three-dimensional structures are generated in the second three-dimensional structure generation step S24, the process returns to the locally stable structure acquisition step S14 and a locally stable structure is acquired by the same method. In the energy acquisition step S16, an energy value of the acquired locally stable structure and each dihedral angle are acquired. For example, it is assumed that a steric structure shown in FIG. 15 is obtained as an example of the locally stable structure obtained this time. The energy of this locally stable structure was −63.2096 kcal/mol.

Next, although determination is made in the determination step S18 whether or not a desired structure or a desired number of the most stable structures or the locally stable structures are obtained, this is the second loop and the structure is not obtained, so that the process proceeds to the energy distribution function calculation step S20.

Figure 16:
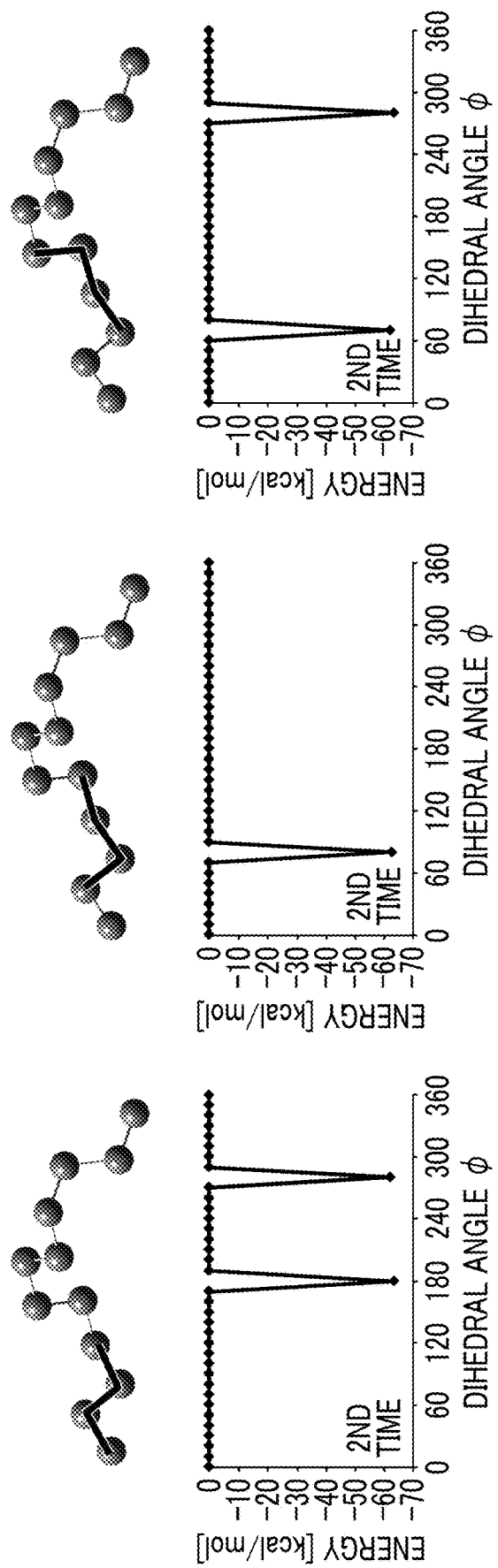
FIG. 16 is a graph showing energy with respect to a dihedral angle that reflects a locally stable structure obtained in the second loop.

FIG. 16 is a graph showing in which an energy value with respect to a dihedral angle of the locally stable structure obtained in the second loop is reflected on the graph of the first loop. In this way, the energy distribution function E(φ) is calculated by reflecting the energy value with respect to the dihedral angle of the newly obtained locally stable structure on the energy distribution function calculated in the previous loop. In a case where the dihedral angle is the same as that in the graph of the first loop, such as the second dihedral angle from the end, an average energy value is used.

Next, in the probability distribution function calculation step S22, a probability distribution function is calculated using the energy distribution function calculated in the energy distribution function calculation step S20 and reflecting the newly obtained locally stable structure. As a method of calculating the probability distribution function, the same method as in the probability distribution function calculation step S22 of the first loop can be used. Since $E_{min}$ in the expression is a value of a structure with lowest energy among the locally stable structures obtained so far, $E_{min}$=−63.2096 kcal/mol, which is an energy value of the locally stable structure shown in FIG. 15 obtained in the second locally stable structure acquisition step S14, is used.

Figure 17:
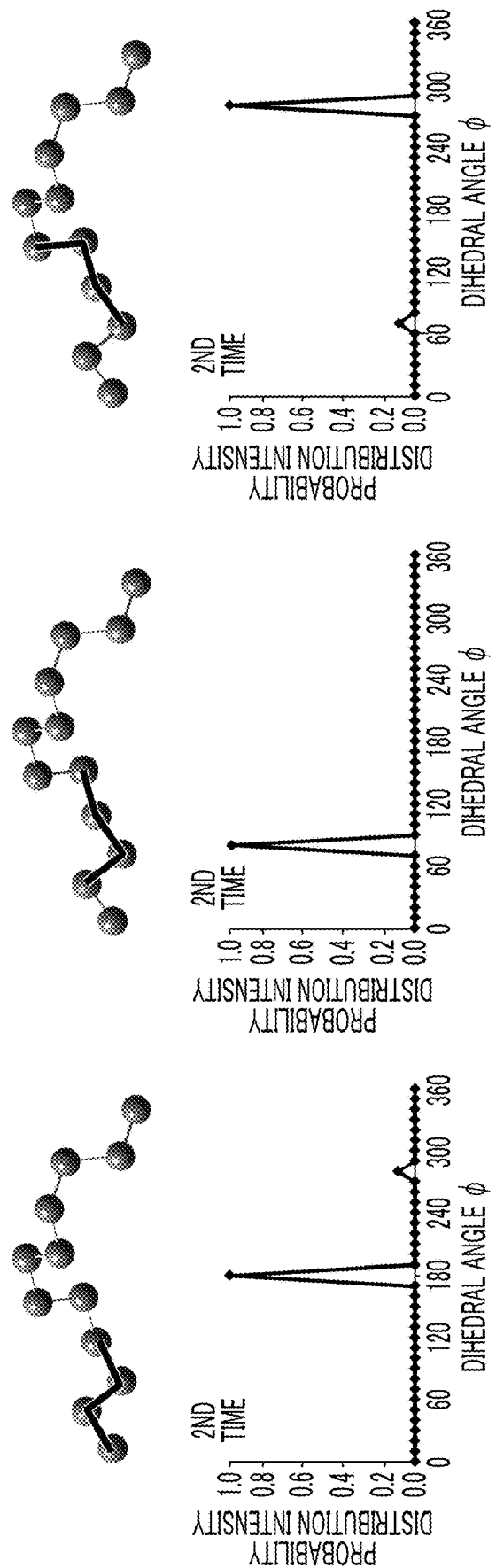
FIG. 17 is a graph showing a probability distribution function $p(\varphi)$ obtained in the second loop.

FIG. 17 is a graph showing a probability distribution function p(φ) obtained in the second loop. Since the energy of the locally stable structure obtained first is −61.8925 kcal/mol, and the energy of the locally stable structure obtained in the second loop is −63.2096 kcal/mol, it is confirmed that internal coordinates of the locally stable structure obtained in the second loop show a high probability distribution intensity.

After that, a three-dimensional structure is generated by using the probability distribution function to acquire a locally stable structure. Although a white noise is not added in FIG. 17, it is preferable that a white noise is added to generate a three-dimensional structure. The dihedral angle and the energy value of the obtained locally stable structure are reflected on the energy distribution function and the probability distribution function, whereby a probability distribution function of increasing a probability of low-energy dihedral angle can be calculated. By repeating these steps, a locally stable structure with lower energy can be acquired. Therefore, it is possible to easily obtain the most stable structure with lowest energy among a plurality of the obtained locally stable structures.

Figure 18:
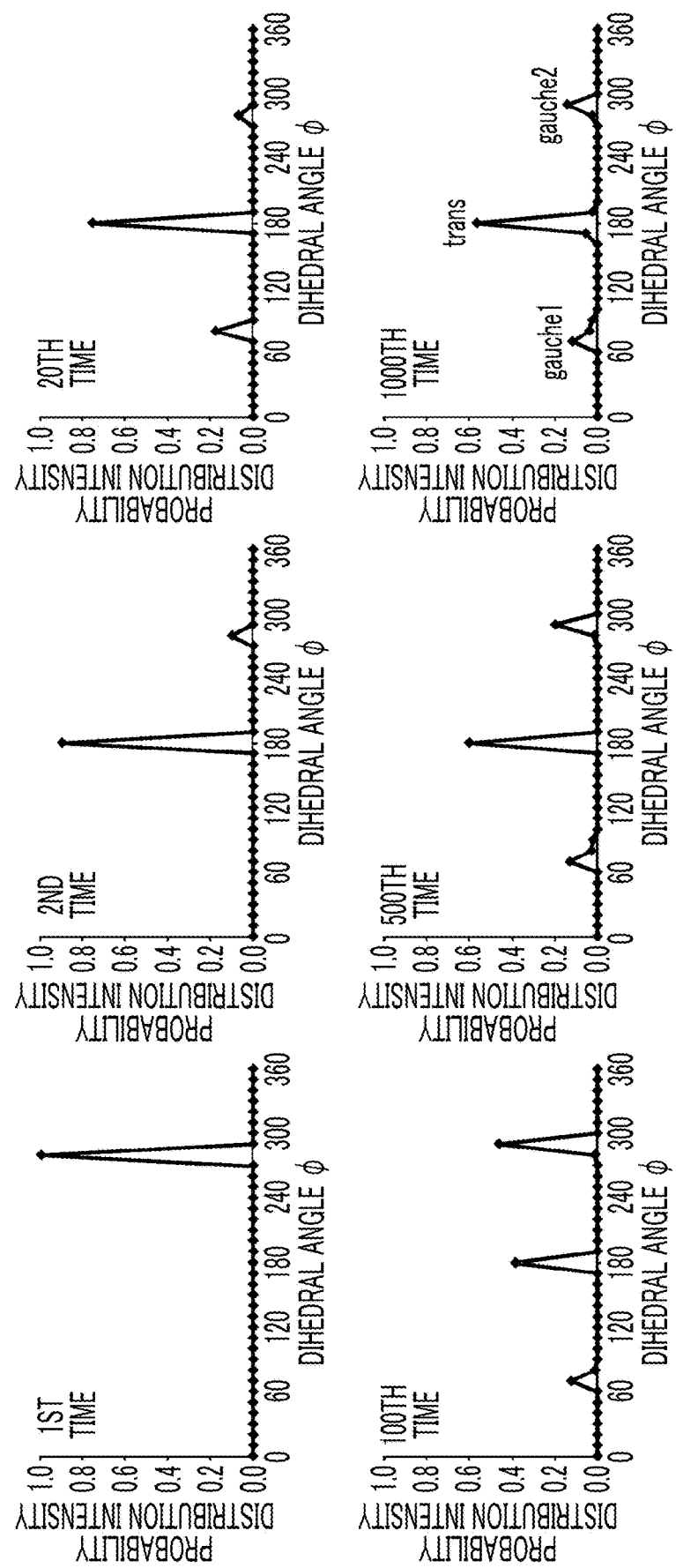
FIG. 18 is a diagram showing changes in probability distribution function $p(\varphi)$ in a case where loop is performed multiple times.

FIG. 18 shows changes in the probability distribution function p(φ) obtained by repeating the second three-dimensional structure generation step S24, the locally stable structure acquisition step S14, the energy acquisition step S16, the energy distribution function calculation step S20, and the probability distribution function S22 with respect to the first dihedral angle from the end of dodecane. It can be confirmed that the structures of the trans type (trans) and the two gauche types (gauche1 and gauche2) are structures with low energy. Further, although the probability distribution intensity is not stable for the trans type and the two gauche types until the number of repetitions is 100 times, the probability distribution intensity is stable at 500 times and 1000 times where the number of repetitions is increased, and thus a probability that a locally stable structure with low energy is obtained can be increased by using these probability distribution functions. Further, from the graph that the number of repetitions is 500 times and 1000 times, it can be confirmed that the trans type is stable as a structure.

FIG. 19 shows changes, according to the number of repetitions, in probability distribution intensities of structures indicated by the trans type (trans) and the two gauche types (gauche1 and gauche2) with respect to the first to third dihedral angles from the end of dodecane (dihedral angle 1, dihedral angle 2, and dihedral angle 3, respectively). It can be confirmed that the trans type is stable for any dihedral angle. In addition, the probability distribution intensity can be stabilized at a constant value by increasing the number of repetitions. Although it is possible to calculate a probability distribution function of obtaining a locally stable structure with low energy by increasing the number of repetitions, in the present embodiment, the purpose is to search for a plurality of locally stable structures and the most stable structure, and therefore, it is not necessary to perform the repetition until the probability distribution intensity is stabilized to a constant value in a case where a desired number of the locally stable structures and the most stable structure are obtained.

Figure 20:
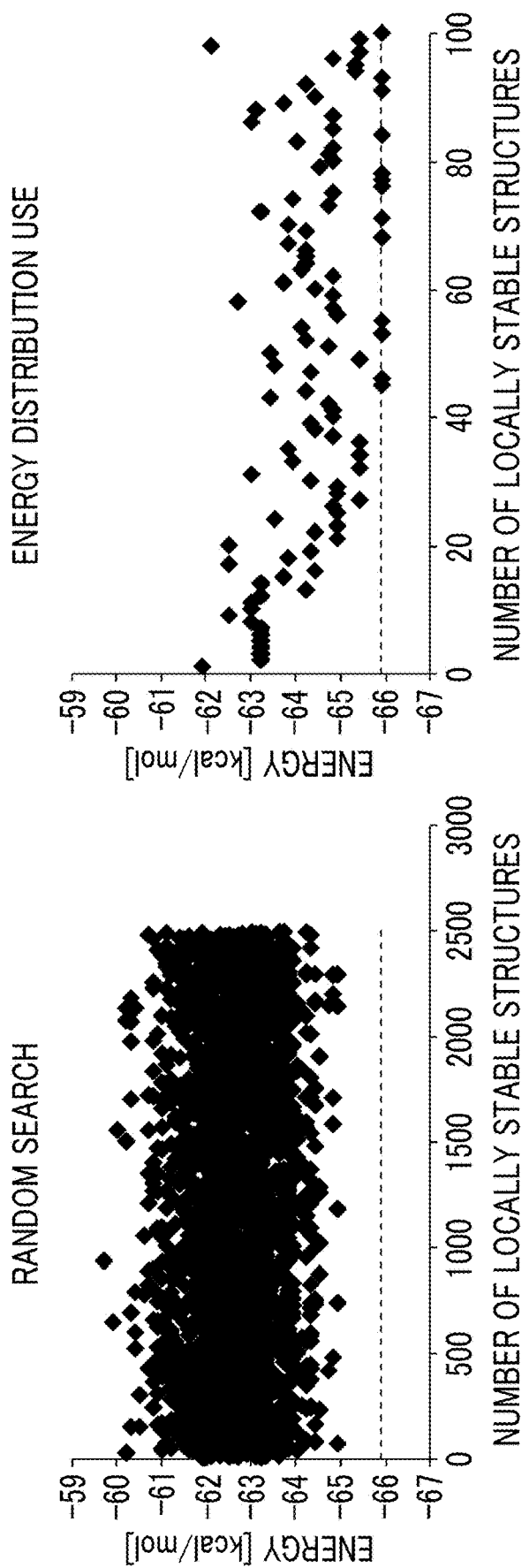
FIG. 20 is a graph showing a relationship between the number of locally stable structures and acquired energy.

FIG. 20 is a graph showing a relationship between the number of locally stable structures acquired and acquired energy in a case of dodecane. Random search is a graph in which energy is obtained and plotted for a structure in which the trans type and the two gauche types as stable structures are randomly selected in a C—C—C—C bond. Energy distribution use is a graph in which a locally stable structure is obtained by using the energy distribution function and the probability distribution function of the present embodiment, and energy of the locally stable structure is obtained and plotted. In dodecane, three stable structures (trans type and two gauche types) exist in one dihedral angle, and nine C—C—C—C bonds exist, and thus, in a case where a three-dimensional structure is randomly generated, structures of $3^9$=19683 are conceivable. The most stable structure is not obtained even though these structures are randomly selected and energy is obtained, or even though search is performed 2500 times as shown in FIG. 20. Further, even at this point of time, in a case where a structure with lowest energy is set as the most stable structure, it is not noticed that there is a structure with lower energy, and the result is erroneous.

With respect to this, according to the search method of the present embodiment, the most stable structure can be discovered in searches of 45 times by reflecting the dihedral angle and energy of the obtained locally stable structure on the probability distribution function. Even after the most stable structure is discovered, the same most stable structure can be rediscovered a plurality of times, and thus, it is possible to reliably obtain the most stable structure, not by chance, with a small number of times.

In the above description, although the method of generating one three-dimensional structure in the first three-dimensional structure generation step S12 and the second three-dimensional structure generation step S24 is described, two or more three-dimensional structures may be generated. In that case, two or more locally stable structures can be obtained. By using the dihedral angle and the energy value of the obtained locally stable structure for calculating the energy distribution function, a highly accurate probability distribution function can be obtained with a small number of repetitions.

Figure 21:
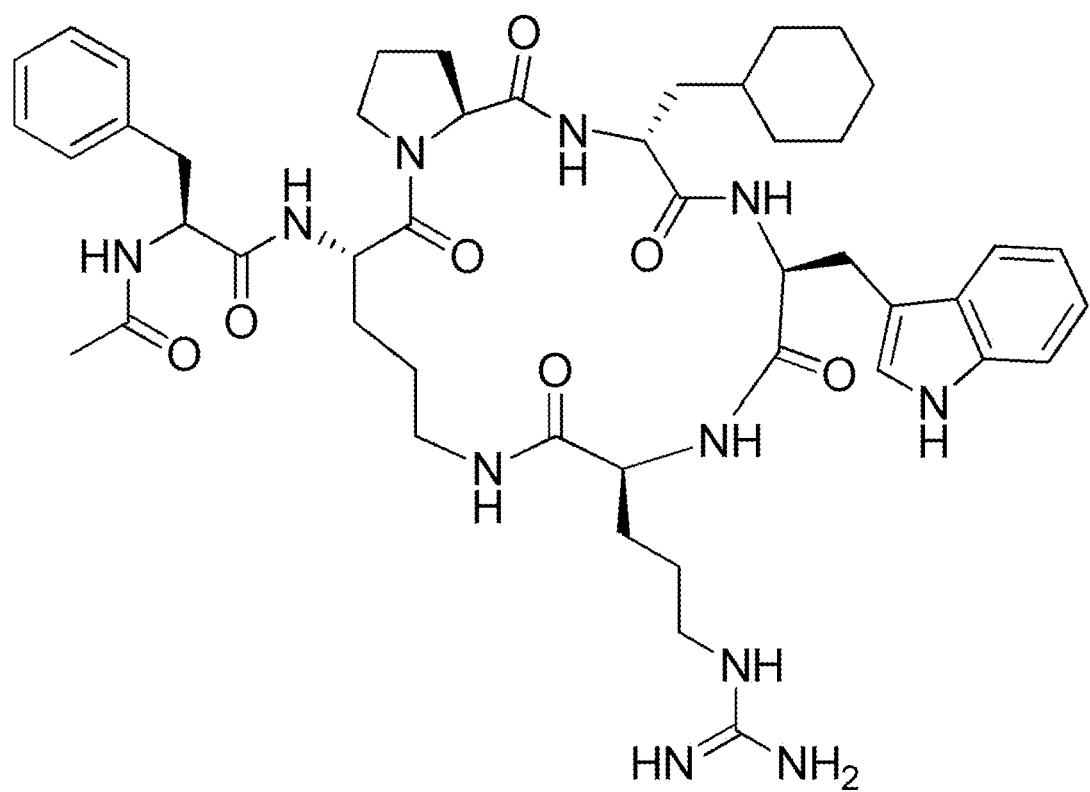
FIG. 21 is a structural formula showing an example of a peptide used in the present embodiment.

Although the above embodiment is described using dodecane for ease of description, the locally stable structure and the most stable structure can be searched for by the same method for a cyclic peptide formed by a plurality of amino acids bonded to one another, which is expected as a drug candidate, as shown in FIG. 21. In the peptide shown in FIG. 21, in a case where the dihedral angle is used as internal coordinates, locally stable structures of $3^{21}$ ($10^{10}$) are conceivable. It is very difficult to randomly generate a structure from these and obtain the most stable structure. According to the present embodiment, the most stable structure can be found with a small number of searches of times, and thus, even in the peptide shown in FIG. 21, a stable structure can be searched for in a short time.

<Output Step (step S26)>

In the determination step S18, in a case where determination is made that a desired number of the locally stable structures are obtained, in a case where determination is made that the most stable structure is obtained, or in a case where determination is made that a desired number of the most stable structures are obtained by repeating the above repetition step, the obtained locally stable structure or most stable structure is output in the output step S26. Although it is considered that the most stable structure with lowest energy is preferable from the viewpoint of the effect of the drug or the membrane permeability, it is preferable to output the locally stable structure in consideration of the other viewpoints, for example, a case where the most stable structure cannot be used as a drug due to the difficulty in formulation. In addition, the characteristics of the three-dimensional structure with low energy can be grasped, which can be useful for future search of the stable structure.

<Effect of Method for Searching for Molecular Stable Structure and Program for Searching for Molecular Stable Structure>

As described above, in the device for searching for a molecular stable structure search device 10, a locally stable structure and the most stable structure of a structural formula of a compound can be searched for in a short time and with high accuracy by using the method for searching for a molecular stable structure and the program for searching for a molecular stable structure according to the present embodiment.

EXPLANATION OF REFERENCES

10: device for searching for molecular stable structure
100: processing unit
105: structural formula acquisition unit
110: three-dimensional structure generation unit
115: locally stable structure acquisition unit
116: most stable structure acquisition unit
120: energy acquisition unit
125: energy distribution function calculation unit
130: probability distribution function calculation unit
135: output unit
140: display control unit
145: CPU
150: ROM
155: RAM
200: storage unit
205: structure information
210: locally stable structure information
215: most stable structure information
220: energy distribution function information
225: probability distribution function information
300: display unit
310: monitor
400: operation unit
410: keyboard
420: mouse
500: external server
510: external database
600: atom
NW: network

What is claimed is:

1. A method for searching for a molecular stable structure, executed by a device comprising a processor, wherein the processor performs:

a structural formula acquisition step of acquiring a structural formula of a compound;

a first three-dimensional structure generation step of generating one or more three-dimensional structures in which internal coordinates of the structural formula are randomly set;

a locally stable structure acquisition step of changing the internal coordinates of the three-dimensional structure to obtain a locally stable structure which is a structure with low energy;

an energy acquisition step of obtaining internal coordinates of the locally stable structure and energy of the locally stable structure in the internal coordinates;

an energy distribution function calculation step of calculating an energy distribution function which is a one-dimensional or multidimensional energy distribution function calculated for one or a plurality of internal coordinates constituting the compound and shows energy distribution of the locally stable structure with respect to the internal coordinates of the locally stable structure;

a probability distribution function calculation step of calculating a probability distribution function of increasing a probability of low-energy internal coordinates from the energy distribution function;

a second three-dimensional structure generation step of simultaneously changing one or more internal coordinates based on the probability distribution function and generating one or more three-dimensional structures using the determined internal coordinates;

a repetition step of repeating, by using the three-dimensional structure generated in the second three-dimensional structure generation step, the locally stable structure acquisition step, the energy acquisition step, the energy distribution function calculation step, the probability distribution function calculation step, and the second three-dimensional structure generation step; and an output step of outputting, via a display, one or both of a plurality of the locally stable structures obtained in the locally stable structure acquisition step and a structure with lowest energy among the plurality of locally stable structures.

2. The method for searching for a molecular stable structure according to claim 1,
wherein the locally stable structure is a structure having internal coordinates in which, in a case where the internal coordinates of the three-dimensional structure are changed in a direction of decreasing the energy, the energy is not further decreased.

3. The method for searching for a molecular stable structure according to claim 1,
wherein the internal coordinates are determined by a dihedral angle obtained by coordinates of four atoms.

4. The method for searching for a molecular stable structure according to claim 3,
wherein the energy distribution function calculation step is performed for all of the dihedral angles that the compound takes.

5. The method for searching for a molecular stable structure according to claim 1, wherein, in the probability distribution function calculation step, a function of accelerating computation is added to the probability distribution function.

6. The method for searching for a molecular stable structure according claim 1,
wherein, in the second three-dimensional structure generation step, either generating a random number and selecting internal coordinates with a highest probability distribution intensity based on the random number, or determining the internal coordinates by the probability distribution function is selected, and the three-dimensional structure is generated.

7. A non-transitory and tangible computer-readable recording medium that causes a computer to execute the method for searching for a molecular stable structure according to claim 1, in a case where a command stored in the recording medium is read by the computer.

8. A device for searching for a molecular stable structure, comprising:
a processor configured to:
acquire a structural formula of a compound;
generate one or more three-dimensional structures;
change internal coordinates of the three-dimensional structure to obtain a locally stable structure which is a structure with low energy;
obtain internal coordinates of the locally stable structure and energy of the locally stable structure in the internal coordinates;
calculate an energy distribution function which is an energy distribution function calculated for each internal coordinate of each atom constituting the compound and shows energy distribution of the locally stable structure with respect to the internal coordinates of the locally stable structure; and
calculate a probability distribution function of increasing a probability of low-energy internal coordinates from the energy distribution function; and
a display that displays the locally stable structure,
wherein the processor generates the three-dimensional structure based on the acquired structural formula of the compound or the probability distribution function.

9. The device for searching for a molecular stable structure according to claim 8, wherein the processor is further configured to:
acquire a structure with lowest energy from the locally stable structures that are obtained.

10. The device for searching for a molecular stable structure according to claim 8, wherein the device further comprises a non-transitory and tangible computer-readable recording medium, and the processor performs processing by referring the recording medium.

11. The device for searching for a molecular stable structure according to claim 8, wherein the processor acquires the structural formula of a compound via a server and/or a database connected to the device via network.

* * * * *